(12) United States Patent
Masuda et al.

(10) Patent No.: US 12,186,495 B2
(45) Date of Patent: Jan. 7, 2025

(54) MEDICAL MULTI-LUMEN TUBE AND METHOD FOR PRODUCING THE SAME

(71) Applicant: ASAHI INTECC CO., LTD., Seto (JP)

(72) Inventors: Naho Masuda, Seto (JP); Shota Endo, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 837 days.

(21) Appl. No.: 17/206,680

(22) Filed: Mar. 19, 2021

(65) Prior Publication Data

US 2021/0205579 A1  Jul. 8, 2021

Related U.S. Application Data

(63) Continuation of application No. PCT/JP2018/037982, filed on Oct. 11, 2018.

(51) Int. Cl.
*A61M 25/00* (2006.01)

(52) U.S. Cl.
CPC .... *A61M 25/0026* (2013.01); *A61M 25/0009* (2013.01); *A61M 25/0045* (2013.01); *A61M 25/0053* (2013.01)

(58) Field of Classification Search
CPC .......... A61M 25/0026; A61M 25/0045; A61M 25/0053
See application file for complete search history.

(56) References Cited

U.S. PATENT DOCUMENTS

| | | | |
|---|---|---|---|
| 5,891,090 A | 4/1999 | Thornton | |
| 9,192,742 B2 | 11/2015 | Pursley | |
| 9,326,729 B2 | 5/2016 | Mori | |
| 2011/0295217 A1* | 12/2011 | Tanaka | A61M 25/0045 |
| | | | 264/209.8 |
| 2018/0015248 A1 | 1/2018 | Logan et al. | |
| 2018/0056032 A1* | 3/2018 | Shimizu | A61M 25/005 |
| 2019/0134348 A1 | 5/2019 | Wada | |

FOREIGN PATENT DOCUMENTS

| | | | |
|---|---|---|---|
| JP | H09-192235 A | | 7/1997 |
| JP | 2001-269411 A | | 10/2001 |
| JP | 2006-034578 A | | 2/2006 |
| JP | 2006-333966 A | | 12/2006 |
| JP | 2008-092969 A | | 4/2008 |
| JP | 2008-229160 A | | 10/2008 |
| JP | 2010-162290 A | | 7/2010 |
| JP | 4854458 B2 | | 1/2012 |
| JP | 2013-138809 A | | 7/2013 |
| JP | 2014-18531 A | | 2/2014 |
| JP | 2014188216 A | * | 10/2014 |
| JP | 2014-530073 A | | 11/2014 |
| JP | 2017-202042 A | | 11/2017 |
| WO | 2017/149974 A1 | | 9/2017 |

\* cited by examiner

*Primary Examiner* — Nathan R Price
*Assistant Examiner* — Tania Ismail
(74) *Attorney, Agent, or Firm* — Oliff PLC

(57) ABSTRACT

A medical multi-lumen tube includes a plurality of inner layer tubes and an outer layer tube covering the plurality of inner layer tubes. The outer layer tube has a first region and a second region placed in the axial direction of the outer layer tube and formed of resins having properties different from each other, and the resin of one of the regions enters the other region, so as to form a wave pattern in a joint part between the first region and the second region.

6 Claims, 17 Drawing Sheets

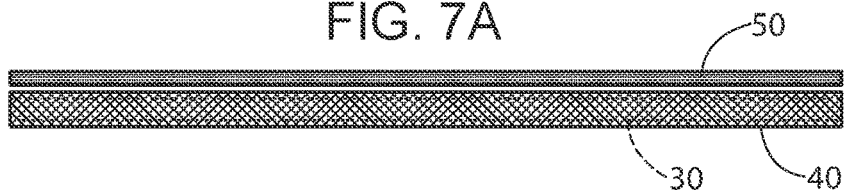
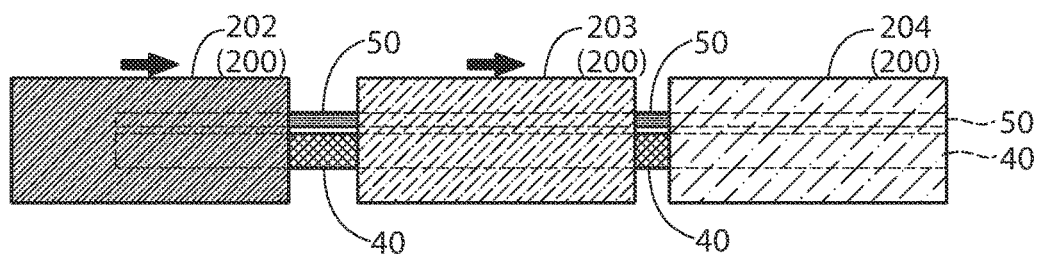
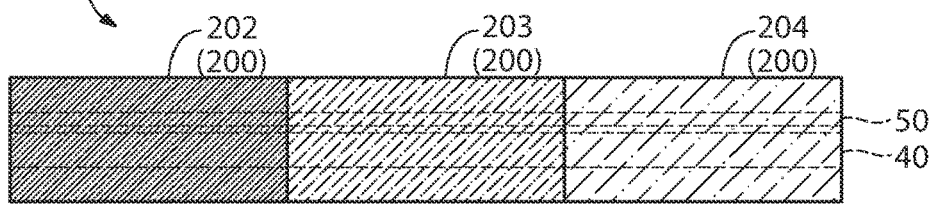
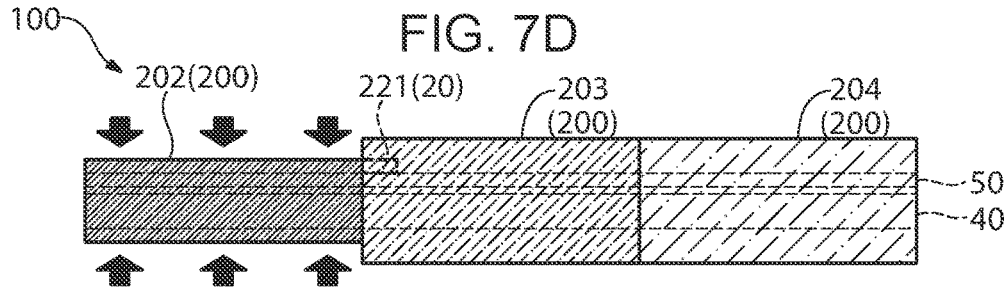
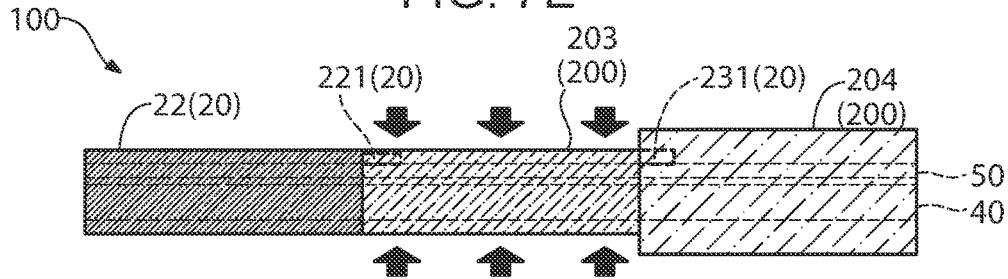
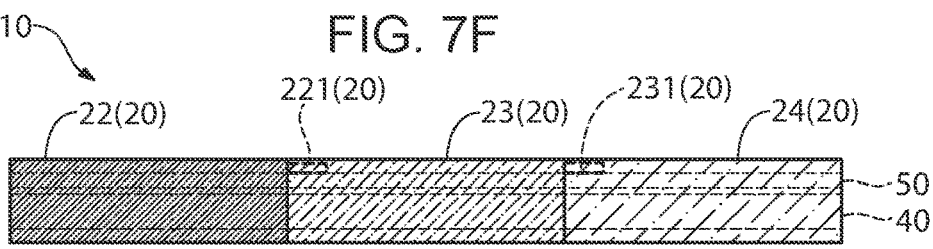

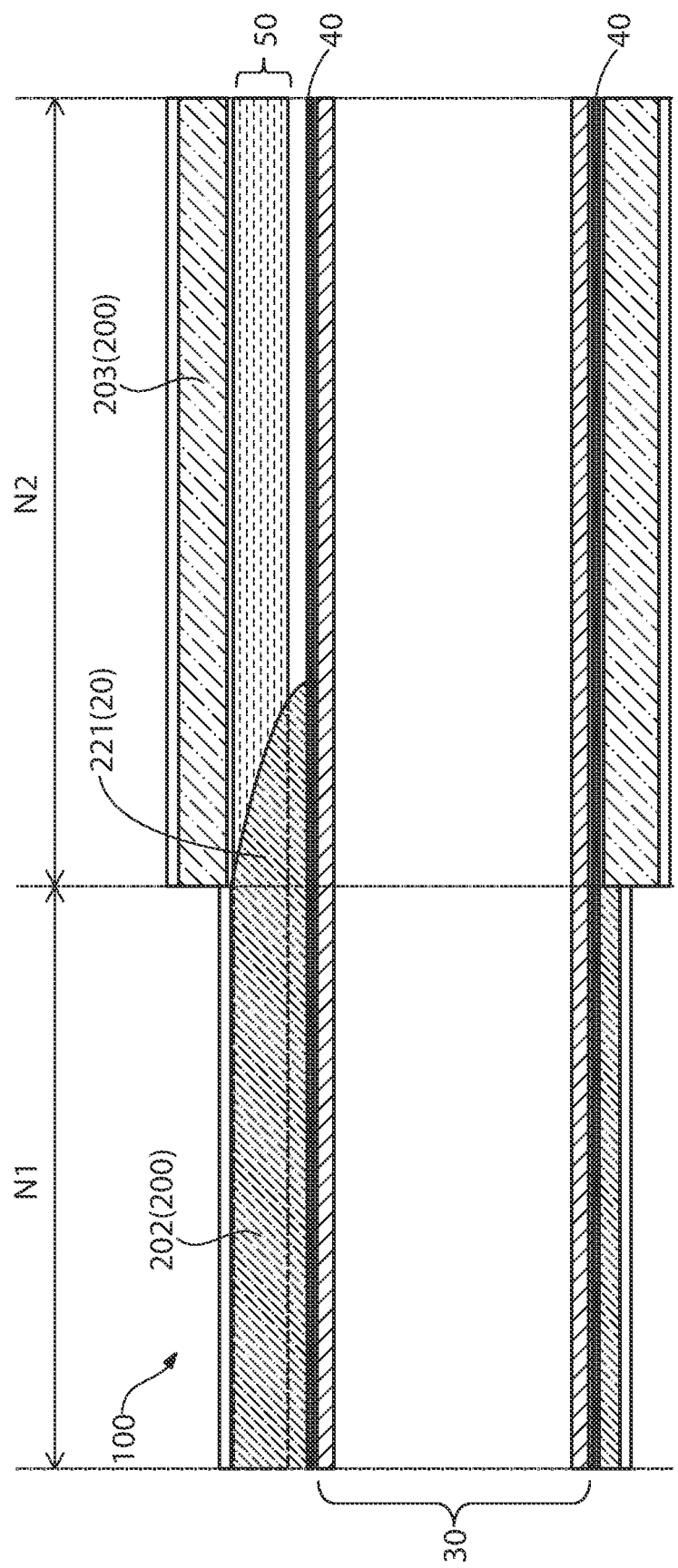

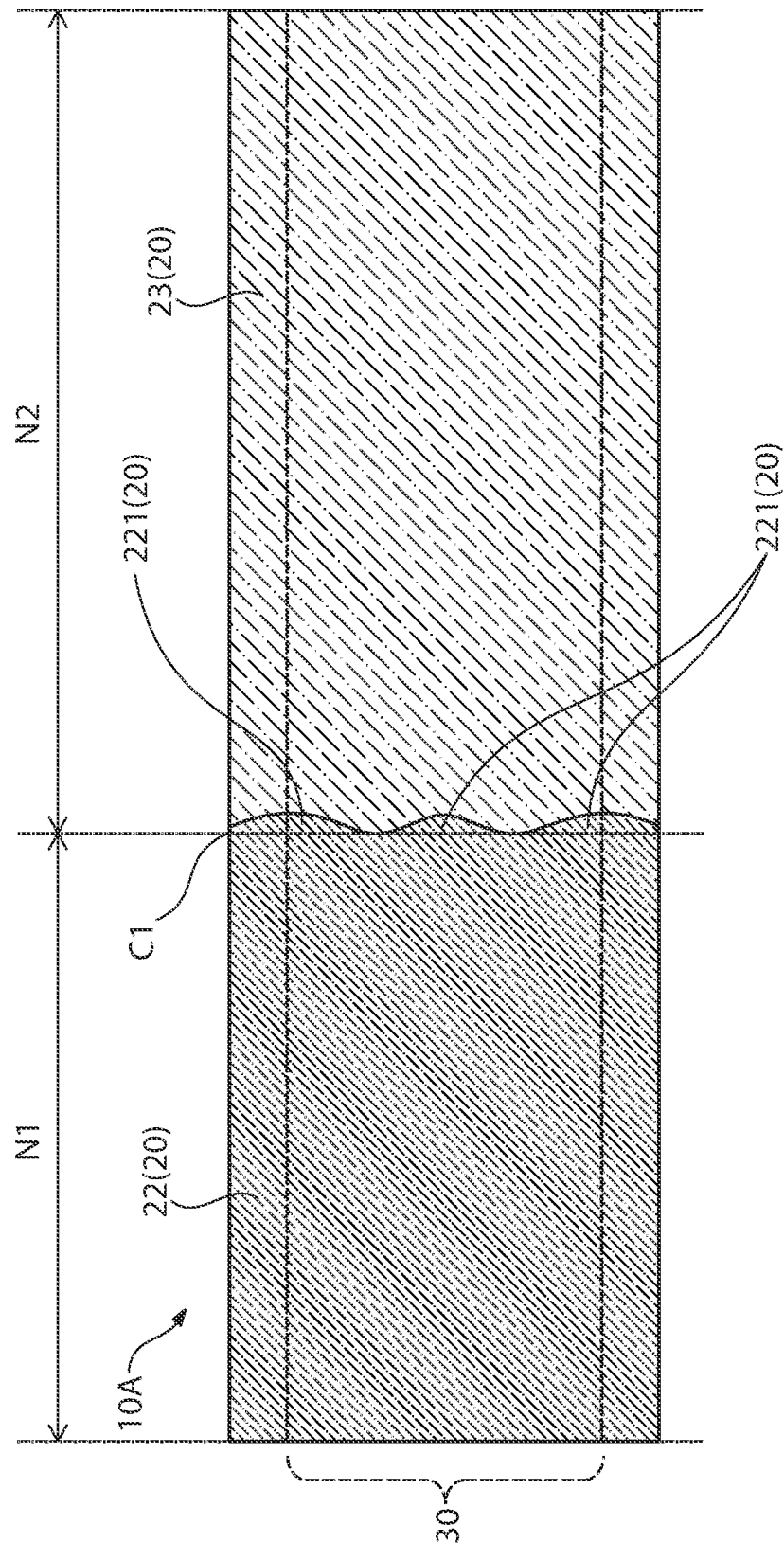

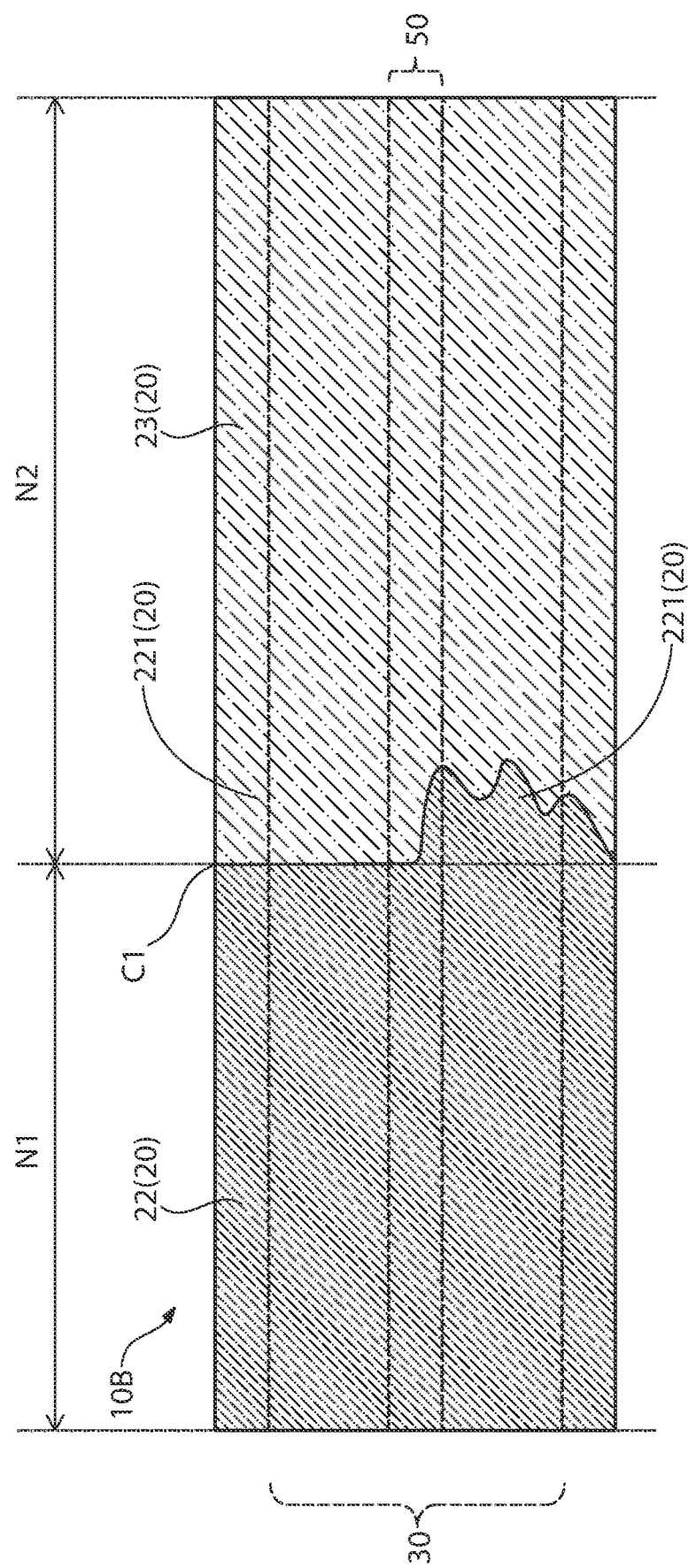

MEDICAL MULTI-LUMEN TUBE AND METHOD FOR PRODUCING THE SAME

CROSS REFERENCE TO RELATED APPLICATION

This is a Continuation of Application No. PCT/JP2018/037982 filed Oct. 11, 2018. The disclosure of the prior application is hereby incorporated by reference herein in its entirety.

TECHNICAL FIELD

The disclosed embodiments relate to a medical multi-lumen tube and a method for producing the same.

BACKGROUND

Conventionally, a medical multi-lumen tube including a plurality of lumens has been known. Multi-lumen tubes are used for catheters, endoscopes, etc., and are inserted into tubular organs of a human body such as blood vessels, digestive tracts, and ureters, and body tissues. For example, Patent Literature 1 discloses a multi-lumen tube including a first lumen inside an inner tube and a second lumen between the outside of the inner tube and the inside of the outer tube. Further, for example, Patent Literature 2 discloses a multi-lumen tube having four lumens. Further, for example, Patent Literature 3 discloses a multi-lumen tube in which a groove portion is formed on the outer peripheral surface of a tubular body forming a main lumen and a hollow tube forming a sub-lumen is disposed in the groove portion.

It is known that a multi-lumen tube is formed by joining resins having different properties to each other in an outer layer. In such a multi-lumen tube, if the joint strength of the joint part is not sufficient, the outer layer may break at the joint part in the blood vessel or the branched blood vessel portions of a winding and complicated route. Further, such a multi-lumen tube is problematic in that a rigidity gap is easily formed leading to a change in flexural rigidity in the vicinity of the joint part, and stress is concentrated in the vicinity of the joint part in the blood vessel or the branched blood vessel portions, and kinking or breakage is likely to occur.

CITATION LIST

Patent Literature

Patent Literature 1: Japanese Unexamined Patent Publication No. 9-192235
Patent Literature 2: Japanese Unexamined Patent Publication No. 2014-18531
Patent Literature 3: Japanese Unexamined Patent Publication No. 2013-138809

SUMMARY

The disclosed embodiments have been devised to address the above-mentioned problems, and an object thereof is to provide a technique for suppressing the occurrence of breakage or kinking in a multi-lumen tube.

The disclosed embodiments include the following embodiments.

(1) According to one of the disclosed embodiments, a medical multi-lumen tube is provided. The multi-lumen tube includes a plurality of inner layer tubes and an outer layer covering the plurality of inner layer tubes. The outer layer has a first region and a second region formed of resins having different properties from each other and placed in the axial direction of the outer layer. In the joint part between the first region and the second region, the resin of one of the regions enters the other region, so as to form a wave pattern.

According to this configuration, the joint area between the resin of the first region and the resin of the second region of the outer layer can be increased, so that the joint strength at the joint part between the first region and the second region can be improved. Further, between the first region and the second region of the outer layer, the switching from the resin constituting one of the regions to the resin constituting the other region is made gradual, so that the change in flexural rigidity can be gradual. As a result, a rigidity gap of flexural rigidity in the vicinity of the joint part is less likely to occur, so that the occurrence of kinking and breakage can be suppressed.

(2) In the multi-lumen tube of the above embodiment, the plurality of inner layer tubes may include a first inner layer tube having a relatively large outer diameter and a second inner layer tube having a relatively small outer diameter. When the outer layer is divided into a side where the first inner layer tube is located and a side where the second inner layer tube is located along the circumferential direction of the outer layer, the wave pattern may be formed on the side where at least the second inner layer tube is located. According to this configuration, the crush resistance of the second inner layer tube can be further improved. Further, the misalignment of the second inner layer tube at the time of forming the outer layer can be suppressed.

(3) In the outer layer of the multi-lumen tube of the above embodiment, the resin of one of the regions may enter the other region on both sides of the second inner layer tube in the circumferential direction of the outer layer, so that a wave pattern may be formed by the resin having entered on both sides of the second inner layer tube. According to this configuration, the displacement of the second inner layer tube at the time of forming the outer layer can be further suppressed.

(4) In the multi-lumen tube of the above embodiment, the outer layer may have a third region formed of a resin having different properties from those of the resin of the second region, wherein the second region and the third region are connected at a second joint part differing from the above joint part, and in the second joint part, the resin of the second region or the third region enters the other region, so that a wave pattern may be formed. According to this configuration, the joint area between the resin of the second region and the resin of the third region of the outer layer can be increased, so that the joint strength at the second joint part can be improved. Further, the switching from the resin constituting one of the regions to the resin constituting the other region is made gradual between the second region and the third region of the outer layer, so that the rigidity gap of the flexural rigidity in the vicinity of the second joint part can be made hard to occur.

(5) According to another embodiment of the disclosed embodiments, a catheter is provided. This catheter includes the multi-lumen tube of the above embodiment, wherein the first region of the multi-lumen tube is closer to the distal end side of the catheter than the second region, and the hardness of the resin of the first region is lower than the hardness of the resin of the second region. According to this configuration, the rigidity can be gradually increased from the distal end to the proximal end of the catheter, so that the passage of the catheter through a tubular organ such as a blood vessel can be improved.

The disclosed embodiments can be realized in various aspects, for example, in various embodiments, such as a catheter including a multi-lumen tube, a balloon catheter, an endoscope, an apparatus for producing a multi-lumen tube, and a method for producing a multi-lumen tube.

BRIEF DESCRIPTION OF DRAWINGS

FIGS. 7A-7F are explanatory diagrams illustrating the production steps of a multi-lumen tube.

FIG. 9 is an explanatory view illustrating a vertical cross section of an assembly when an outer layer tube is melted.

FIG. 10 is an explanatory view illustrating the multi-lumen tube of the second embodiment.

FIG. 11 is an explanatory view illustrating the multi-lumen tube of the third embodiment.

DETAILED DESCRIPTION OF EMBODIMENTS

First Embodiment

Figure 1:
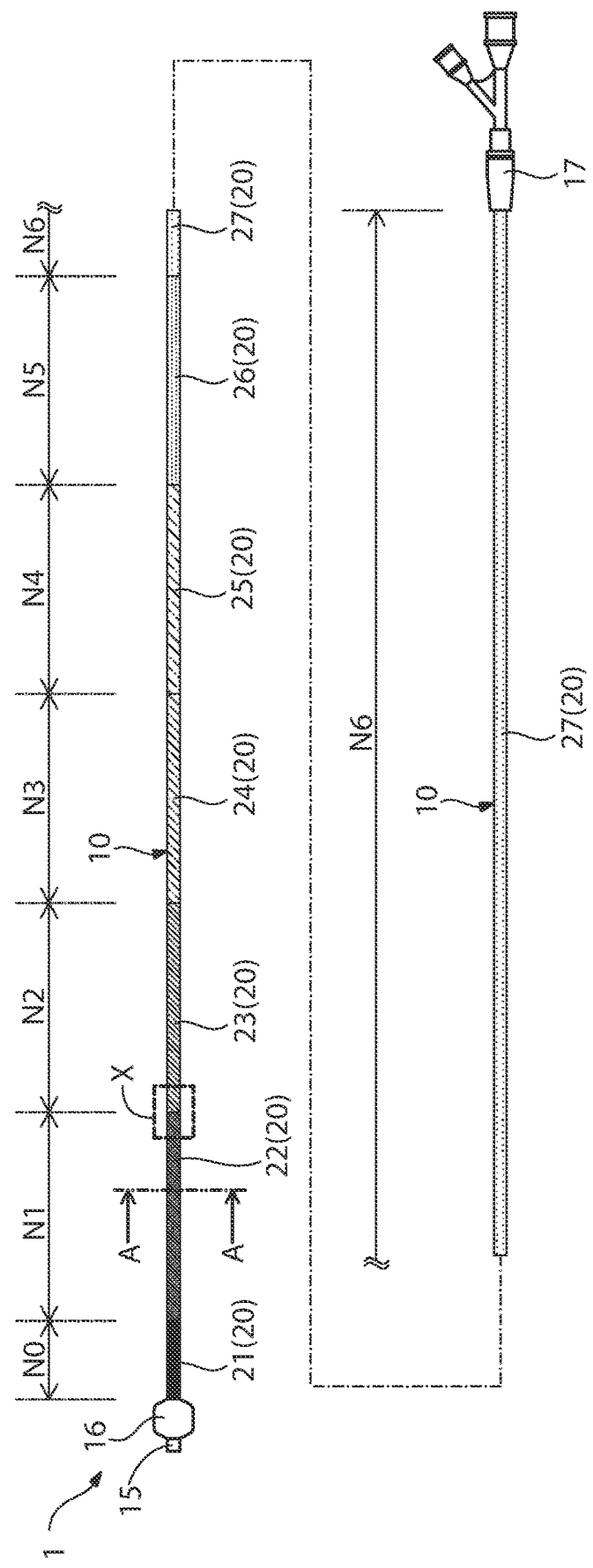
FIG. 1 is an explanatory view illustrating the appearance of a catheter of the first embodiment.
Figure 2:
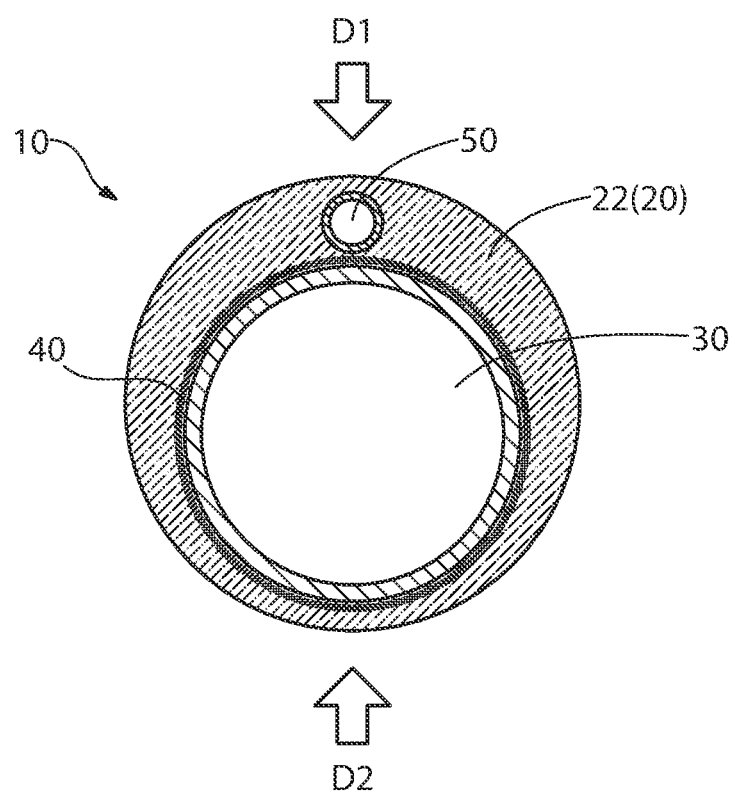
FIG. 2 is an explanatory view illustrating a cross section taken along the line A-A of FIG. 1.

The overall configuration of a catheter 1 including a multi-lumen tube 10 of the first embodiment will be described with reference to FIGS. 1 and 2. FIG. 1 is an explanatory view illustrating the appearance of the catheter 1. FIG. 2 is an explanatory view illustrating a cross section taken along the line A-A in FIG. 1 in the multi-lumen tube 10. Hereinafter, the left side (distal tip 15 side) of FIG. 1 is referred to as the "distal end side" of the catheter 1, and the right side (connector 17 side) of FIG. 1 is referred to as the "proximal end side" of the catheter 1. The distal end side of the catheter 1 is the side (distal side) to be inserted into the body, and the proximal end side of the catheter 1 is the side (proximal side) to be operated by a technician such as a doctor. The catheter 1 is used for diagnosing or treating a constricted part or an obstruction part. For example, the catheter 1 is inserted into a blood vessel of a heart in which a constricted part is formed and then used to expand the intravascular constricted part.

As shown in FIG. 1, the catheter 1 includes the multi-lumen tube 10, the distal tip 15, a balloon 16, and a connector 17, and is configured here as a balloon catheter. As shown in FIGS. 1 and 2, the multi-lumen tube 10 is a long member having two lumens inside, and has an outer layer 20, a first inner layer tube 30, a reinforcing body 40, and a second inner layer tube 50. The distal tip 15 is provided at the distal end of the catheter 1 and has an opening (not shown) that communicates with the first inner layer tube 30. The balloon 16 is provided between the multi-lumen tube 10 and the distal tip 15, and the internal space of the balloon 16 communicates with the second inner layer tube 50. The connector 17 is connected to the proximal end of the multi-lumen tube 10 and has an opening (not shown) that communicates with the first inner layer tube 30 and the second inner layer tube 50. As an example, the catheter 1 can be used to take out a guide wire or another catheter inserted through the opening of the connector 17 from the opening of the distal tip 15 via the inside of the first inner layer tube 30. Further, the catheter 1 can be used to supply a fluid from the opening of the connector 17 to the internal space of the balloon 16 via the second inner layer tube 50.

The first inner layer tube 30 is a tube formed of a resin, wherein a lumen into which a guide wire or another catheter is inserted is formed inside. Resin materials for forming the first inner layer tube 30 are not particularly limited. Examples thereof can include PTFE (polytetrafluoroethylene), PVDF (polyvinylidene fluoride), PFA (perfluoroalkoxy alkane), FEP (perfluoroethylene propene), ETFE (ethylene tetrafluoroethylene), PE (polyethylene), and PP (polypropylene). The outer diameter of the first inner layer tube 30 is configured to be larger than the outer diameter of the second inner layer tube 50.

The reinforcing body 40 is a braided body (metal blade layer) in which the first wire and the second wire are woven into each other in a mesh shape, is disposed on the outer periphery of the first inner layer tube 30, and is covered (buried) by an outer layer 20. The reinforcing body 40 may cover the entire first inner layer tube 30, or may cover a part of the first inner layer tube 30.

The second inner layer tube 50 is a tube formed of a resin, and a lumen for flowing a fluid is formed inside. The resin material forming the second inner layer tube 50 is not particularly limited. The second inner layer tube 50 may be formed of the same type of resin as that of the first inner layer tube 30 or a type of resin different from that of the first inner layer tube 30. The outer diameter of the second inner layer tube 50 is configured to be smaller than the outer diameter of the first inner layer tube 30.

The outer layer 20 is formed of a resin and covers the first inner layer tube 30, the reinforcing body 40, and the second inner layer tube 50. The outer layer 20 is formed by placing seven types of resins having different properties from each other in the axial (longitudinal) direction and joining resins adjacent to each other, thereby having 7 regions (N0 to N6) formed of different resins. The resin material forming each region of the outer layer 20 is not particularly limited, and examples thereof can include polyamide, polyamide elastomer, polyester, polyurethane, and polyurethane elastomer. Further, the resins forming the outer layer 20 may contain tungsten powder, and the hardness of the resins may be changed depending on the contents thereof. The resins forming the outer layer 20 can contain tungsten powder that is a radiation-impermeable powder, so that a technician such as a doctor can accurately grasp the position of the catheter 1 at the time of coronary angiography.

Here, in the outer layer 20, regions formed of resins having different properties from each other are also referred to as, in order from the distal end side to the proximal end side of the outer layer 20, the distal end region N0, the first region N1, the second region N2, the third region N3, the fourth region N4, the fifth region N5, and the sixth region N6. The distal end side of the distal end region N0 of the outer layer 20 is connected to the proximal end side of the balloon 16, and the proximal end side of the distal end region N0 is connected to the distal end side of the first region N1. The distal end side of the second region N2 of the outer layer 20 is connected to the proximal end side of the first region N1, and the proximal end side of the second region N2 is connected to the distal end side of the third region N3. In the outer layer 20, the distal end side of the fourth region N4 is connected to the proximal end side of the third region N3, and the proximal end side of the fourth region N4 is connected to the distal end side of the fifth region N5. In the outer layer 20, the distal end side of the sixth region N6 is connected to the proximal end side of the fifth region N5, and the proximal end side of the sixth region N6 is connected to the connector 17.

The outer layer 20 is configured so that the hardness H0 of a resin 21 forming the distal end region N0, the hardness H1 of a resin 22 forming the first region N1, the hardness H2 of a resin 23 forming the second region N2, the hardness H3 of a resin 24 forming the third region N3, the hardness H4 of a resin 25 forming the fourth region N4, the hardness H5 of a resin 26 forming the fifth region N5, and the hardness H6 of a resin 27 forming the sixth region N6 satisfy the following formula (1).

$$H0<H1<H2<H3<H4<H5<H6 \qquad (1)$$

That is, the catheter 1 is configured so that the hardness of the resins of the outer layer 20 increases from the distal end side to the proximal end side. This makes it possible to improve the passage of the catheter 1 through a tubular organ such as a blood vessel.

In general, it is preferable that the flexural rigidity of a catheter gradually increases from the distal end portion to the proximal end portion. The distal end portion has relatively high flexibility, making it possible to hardly damage the inner surface of the blood vessel even in a vessel bifurcation at a steep angle. On the other hand, the proximal end portion has relatively high rigidity, making it possible to enhance the torque transmissibility for transmitting the rotational movement of the catheter by the operator to the distal end portion side. Further, making the change in the rigidity of a catheter in the axial direction at a level as constant as possible can suppress the occurrence of kinking etc., due to the rigidity gap. Therefore, the catheter having flexural rigidity gradually increasing from the distal end portion to the proximal end portion can improve the passage of the catheter 1 through a tubular organ such as a blood vessel.

In the present embodiment, the "hardness of the resin" is not limited to the hardness of the resin itself, but means the entire hardness including the hardness of the resin itself plus the hardness of the material to be kneaded with the resin. Therefore, a method for varying the hardness of resins is not limited to varying the resin types. The hardness of resins can also be varied by varying the amount of the material to be kneaded with the same type of resin.

Figure 3:
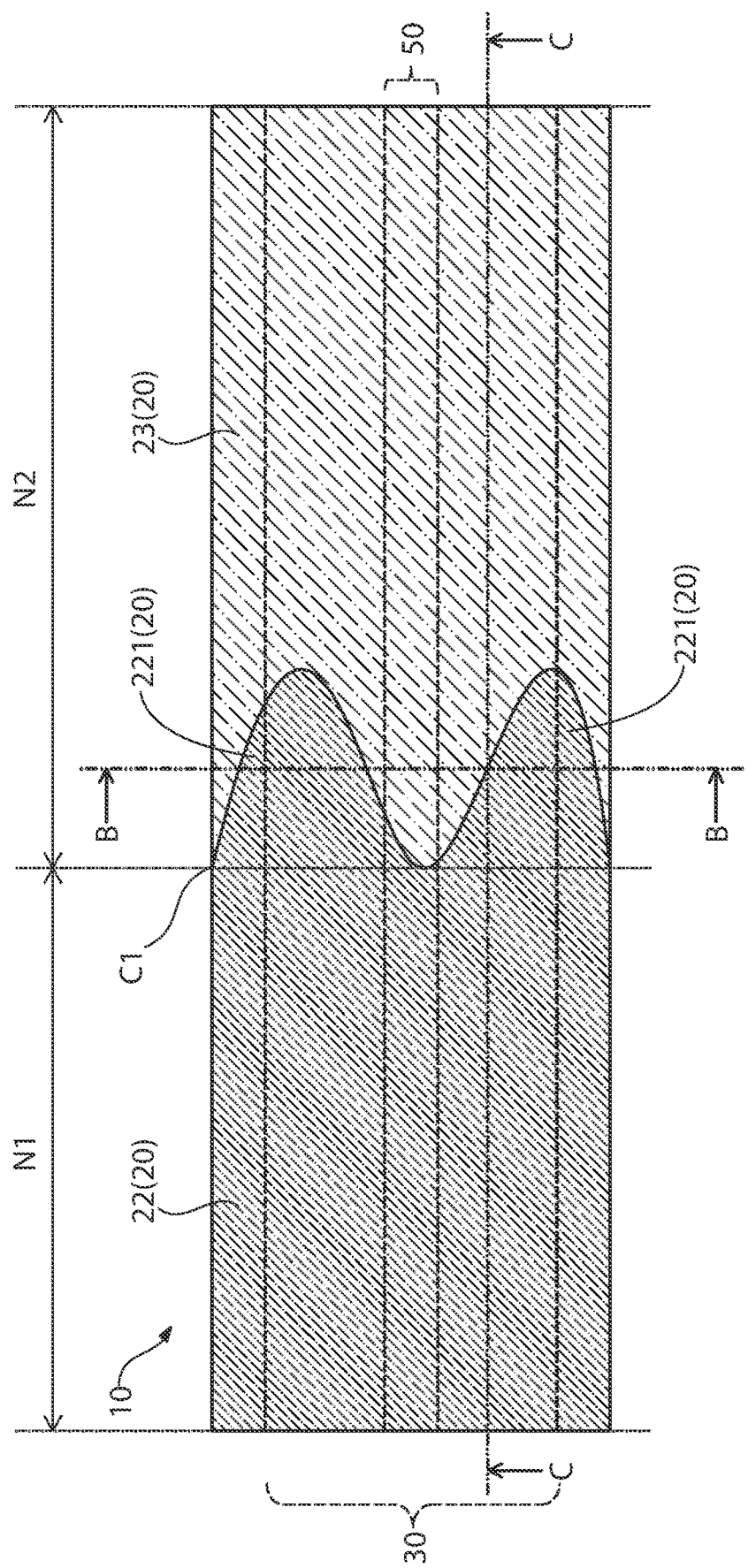
FIG. 3 is an explanatory view of the X portion in FIG. 1 as viewed from the D1 direction in FIG. 2.
Figure 4:
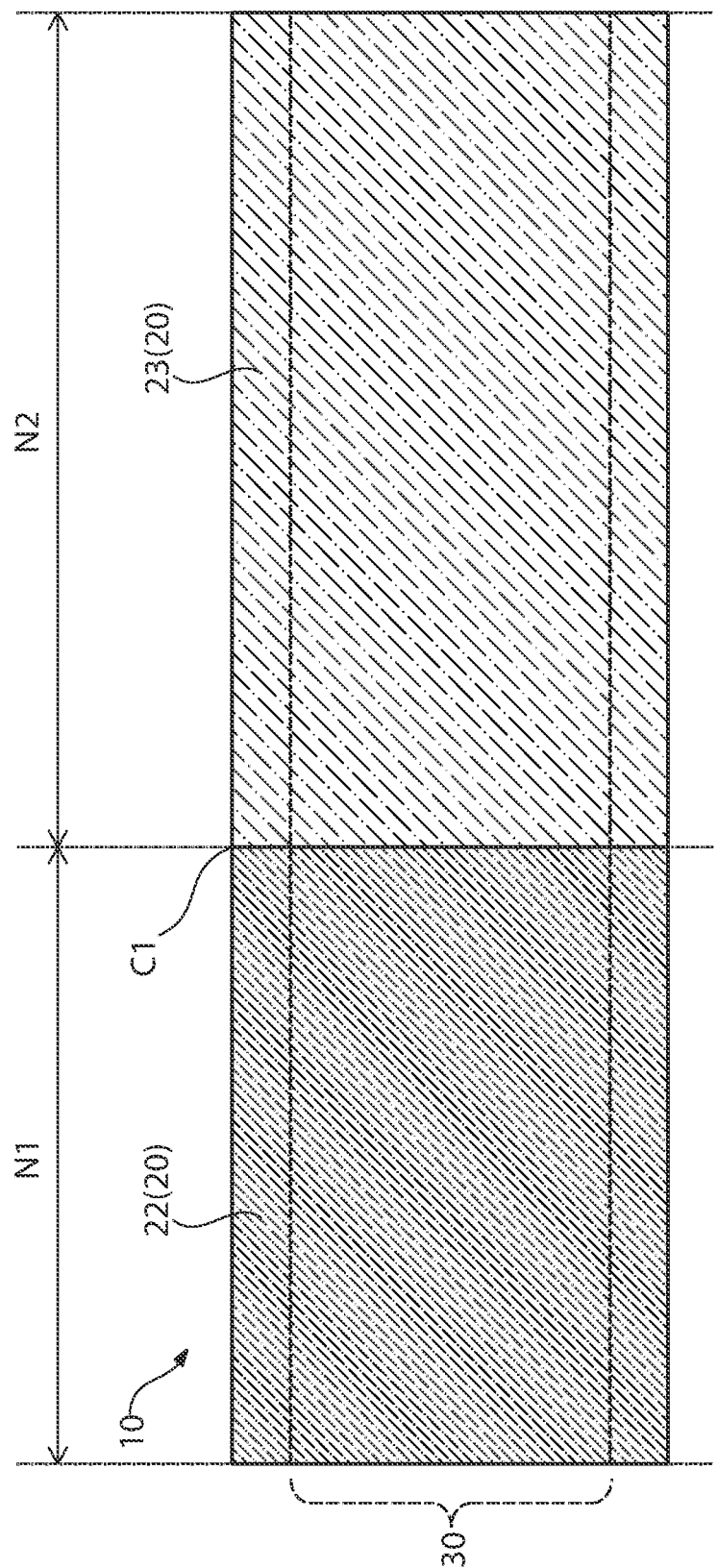
FIG. 4 is an explanatory view of the X portion in FIG. 1 as viewed from the D2 direction in FIG. 2.

The configuration in the vicinity of the joint part between the first region N1 and the second region N2 of the outer layer 20 will be described with reference to FIGS. 3 to 6. FIG. 3 is an explanatory view of the X portion in FIG. 1 of the multi-lumen tube 10 as viewed from the D1 direction in FIG. 2. FIG. 4 is an explanatory view of the X portion in FIG. 1 of the multi-lumen tube 10 as viewed from the D2 direction of FIG. 2. In FIG. 2, when the outer surface of the outer layer 20 is divided into an upper side (second inner layer tube 50 side) and a lower side (first inner layer tube 30 side), FIG. 3 shows a half on the upper side of the outer surface of the outer layer 20. FIG. 4 shows a half on the lower side of the outer surface of the outer layer 20. In other words, when the outer layer 20 is divided into a side where the first inner layer tube 30 is located and a side where the second inner layer tube 50 is located along the circumferential direction of the outer layer 20, FIG. 3 shows the side where the second inner layer tube 50 is located (the second inner layer tube 50 side of the outer layer 20), and FIG. 4 shows the side where the first inner layer tube 30 is located (the first inner layer tube 30 side of the outer layer 20).

As shown in FIG. 3, on the second inner layer tube 50 side of the outer layer 20, the resin 22 of the first region N1 enters the second region N2 in the joint part C1 between the first region N1 and the second region N2, so as to form a wave pattern. A portion of the resin 22 having entered the second region N2 is also referred to as an entering resin 221. The entering resin 221 is provided on both sides of the second inner layer tube 50 in the circumferential direction of the outer layer 20. In other words, in the outer layer 20, the resin 22 of the first region N1 has entered the second region N2 on both sides of the second inner layer tube 50 in the circumferential direction of the outer layer 20, so that a wave pattern is formed by the resin 22 having entered on both sides of the second inner layer tube 50. The wave pattern may be formed by: the alternate repetition of a portion with the entering resin 221 and a portion without the entering resin 221; or varied distances the entering resin 221 has entered in the circumferential direction of the outer layer 20 (a change of the end edge position the entering resin 221).

As shown in FIG. 4, on the first inner layer tube 30 side of the outer layer 20, the resin 22 of the first region N1 has not substantially entered the second region N2 in the joint part C1 between the first region N1 and the second region N2, so as to form no wave pattern. Therefore, the boundary between the first region N1 and the second region N2 is substantially linear along the circumferential direction of the outer layer 20. In addition, also on the first inner layer tube 30 side of the outer layer 20, a wave pattern may be formed by the resin 22 of the first region N1 having entered the second region N2 in the joint part C1 between the first region N1 and the second region N2, similarly to the second inner layer tube 50 side (FIG. 3) of the outer layer 20.

Figure 5:
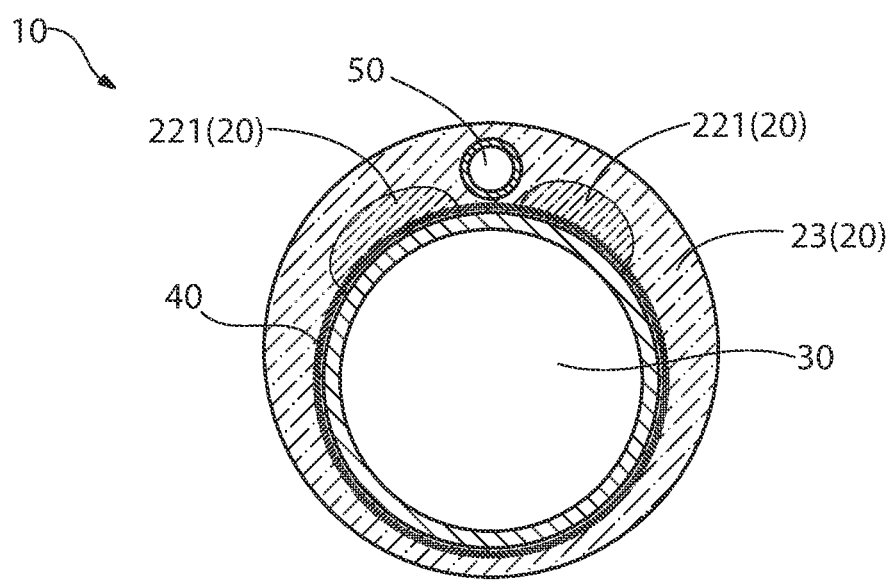
FIG. 5 is an explanatory view illustrating a cross section taken along the line B-B in FIG. 3.
Figure 6:
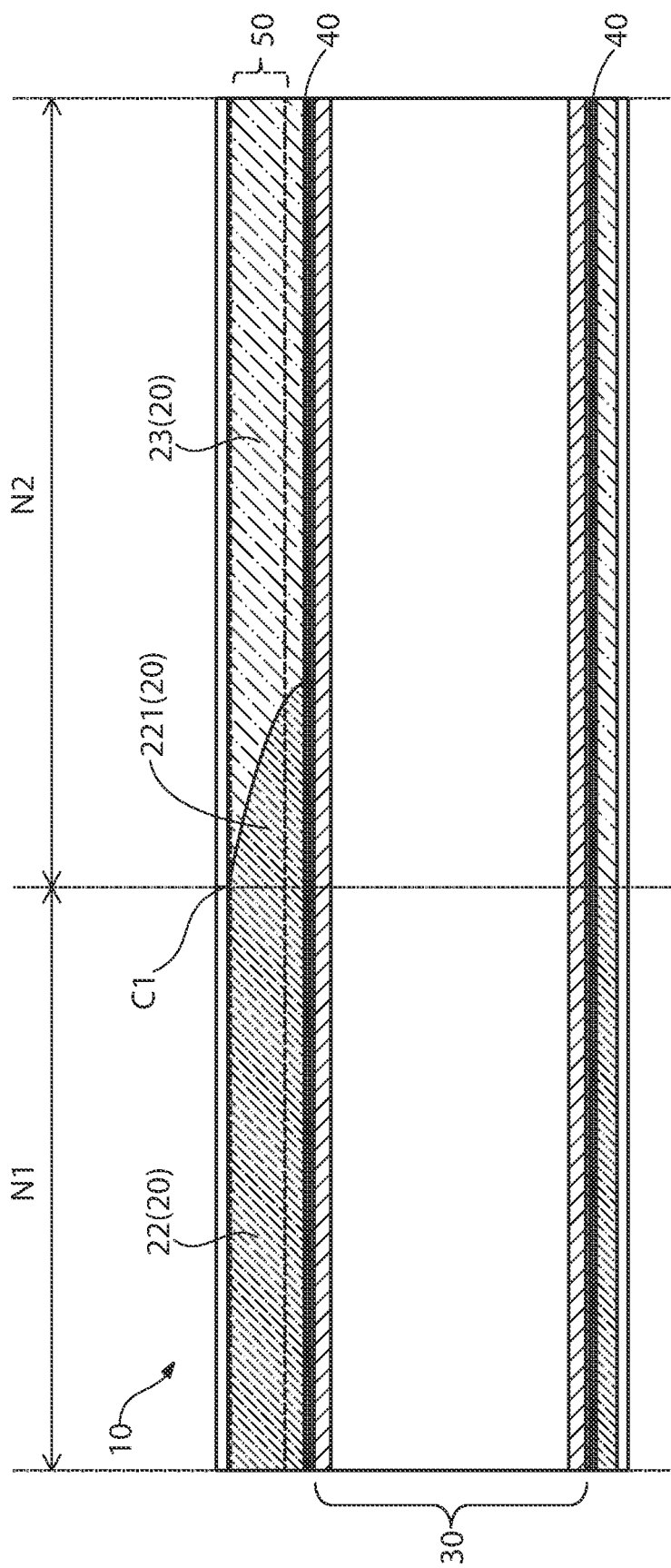
FIG. 6 is an explanatory view illustrating a cross section taken along the line C-C in FIG. 3.

FIG. 5 is an explanatory view illustrating a cross section taken along the line B-B of FIG. 3 in the multi-lumen tube 10. FIG. 6 is an explanatory view illustrating a cross section taken along the line C-C of FIG. 3 in the multi-lumen tube 10. As shown in FIG. 5, the entering resin 221 having entered the second region N2 is located on both sides of the second inner layer tube 50 and is in contact with the reinforcing body 40 and the first inner layer tube 30. Further, the entering resin 221 is covered by the resin 23. On the outer surface of the outer layer 20, the entering resin 221 can be visually recognized through the resin 23. As shown in FIG. 6, the entering resin 221 having entered the second region N2 of the outer layer 20 is formed by flowing of the resin 22 of the first region N1 into the second region N2 side at the time of producing the multi-lumen tube 10 described later. Therefore, the entering resin 221 becomes thinner (toward the proximal end direction) as the distance from the first region N1 to the second region N2 increases.

A method for producing the multi-lumen tube 10 will be described with reference to FIGS. 7A to 9. FIGS. 7A-7F illustrate the production steps of the multi-lumen tube 10. In producing the multi-lumen tube 10, first, as shown in FIG. 7A, the first inner layer tube 30 in which the reinforcing body 40 is disposed on the outer periphery and the second inner layer tube 50 are prepared. Next, as shown in FIG. 7B, outer layer tubes 200 are disposed outside the prepared first inner layer tube 30 and the second inner layer tube 50. The outer layer tubes 200 are tubular members formed of resins that are raw materials of the outer layer 20, and are prepared for each type of resin of the outer layer 20. Here, an outer layer tube (not shown) formed of the resin 21 of the distal end region N0, an outer layer tube 202 formed of the resin 22 of the first region N1, an outer layer tube 203 formed of the resin 23 of the second region N2, an outer layer tube 204 formed of the resin 24 of the third region N3, an outer layer tube (not shown) formed of the resin 25 of the fourth region N4, an outer layer tube (not shown) formed of the resin 26 of the fifth region N5, and an outer layer tube (not shown) formed of the resin 27 of the sixth region N6 are prepared. The first inner layer tube 30 and the second inner layer tube 50 are sequentially inserted into the prepared seven outer layer tubes 200 to prepare an assembly 100 shown in FIG. 7C.

Figure 8:
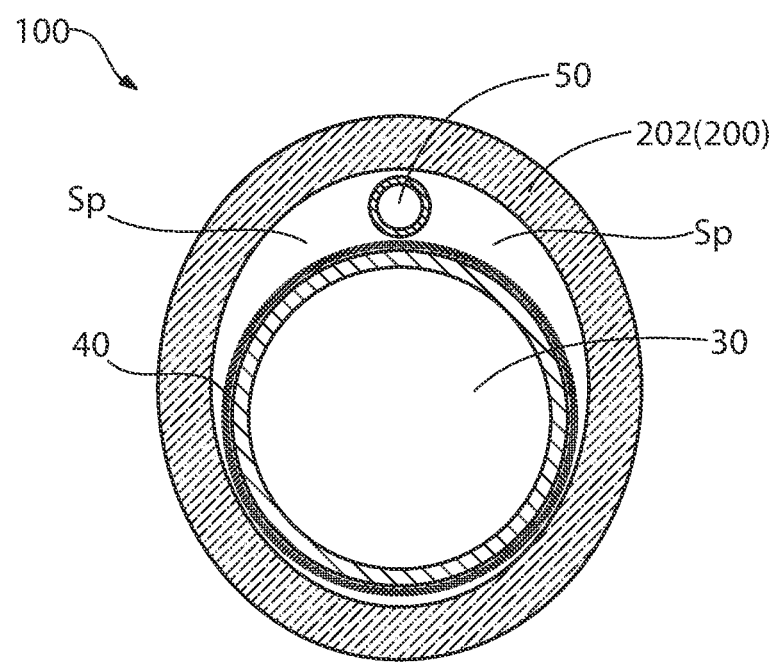
FIG. 8 is an explanatory view illustrating a transverse section of an assembly.

FIG. 8 is an explanatory view illustrating a transverse section of the assembly 100. The inner diameter of the outer layer tubes 200 is larger than the sum of the two outer diameters of the first inner layer tube 30 and the second inner layer tube 50, producing a gap between the outer peripheries of the first inner layer tube 30 and the second inner layer tube 50 housed in the outer layer tubes 200 and the inner periphery of the outer layer tubes 200 in the assembly 100. In particular, the outer diameter of the second inner layer tube 50 is smaller than the outer diameter of the first inner layer tube 30, producing relatively a large gap Sp on both sides of the second inner layer tube 50.

Returning to the discussion of the production method, after preparing the assembly 100 of FIG. 7C, the outer layer tubes 200 are heated from the outside as shown in FIGS. 7D and 7E to melt the resins constituting the outer layer tubes 200 and thus to form the outer layer 20. That is, the outer layer tubes 200 are heated to pour the molten resin between the outer peripheries of the first inner layer tube 30 and the second inner layer tube 50 and the inner periphery of the outer layer tubes 200 and thus to fill the gap. Here, the seven outer layer tubes 200 are heated one by one in order, instead of heating all the tubes 200 simultaneously. As for the order of heating, in the present embodiment, heating is performed in order from the distal end side to the proximal end side. That is, here, the outer layer tube of the distal end region N0 (not shown), the outer layer tube 202 of the first region N1, the outer layer tube 203 of the second region N2, the outer layer tube 204 of the third region N3, the outer layer tube (not shown) of the fourth region N4, the outer layer tube (not shown) of the fifth region N5, and the outer layer tube (now shown) of the sixth region N6 are heated in this order. FIG. 7D shows a state in which the outer layer tube 202 is heated to melt the resin. FIG. 7E shows a state in which the outer layer tube 203 is heated to melt the resin.

FIG. 9 is an explanatory view illustrating a vertical cross section of the assembly 100 when the outer layer tube 202 is melted. When the outer layer tube 202 is heated to melt the resin, a part of the molten resin flows into the inside of the outer layer tube 203 adjacent on the proximal end side. As a result, the entering resin 221 is formed. In particular, relatively a large gap Sp (see FIG. 8) is formed on both sides of the second inner layer tube 50 inside the outer layer tube 203, so that the resin flows into the gap Sp and the relatively large entering resin 221 is formed.

Returning to the discussion of the production method, the outer layer tube 202 is melted to form the first region N1 of the outer layer 20, and then the outer layer tube 203 is heated to melt the resin as shown in FIG. 7E. At this time, a part of the molten resin flows into the inside of the outer layer tube 204 adjacent on the proximal end. As a result, the second region N2 of the outer layer 20 is formed, and the entering resin 231 is formed. In this way, the seven outer layer tubes 200 are heated from the outer layer tube on the distal end side, so that as shown in FIG. 7F, the production of the multi-lumen tube 10 is completed in which the resin of the distal end side region has entered the adjacent proximal end side region. The outer layer 20 of the multi-lumen tube 10 includes a joint part between the distal end region N0 and the first region N1, a joint part between the second region N2 and the third region N3, a joint part between the third region N3 and the fourth region N4, a joint part between the fourth region N4 and the fifth region N5, and a joint part between the fifth region N5 and the sixth region N6, wherein the configuration of each joint part is the same as that of the joint part C1 between the first region N1 and the second region N2 shown in FIGS. 3 and 4.

Examples of the Effects of this Embodiment

According to the multi-lumen tube 10 of the present embodiment described above, the entering resin 221 (FIG. 3) forms a wave pattern in the joint part C1 between the first region N1 and the second region N2 of the outer layer 20, so that the joint area can be increased as compared with a case where the joint part is linear. Accordingly, the joint strength at the joint part C1 between the first region N1 and the second region N2 can be improved. Further, the entering resin 221 is formed to realize the gradual switching from the resin 22 constituting the first region N1 to the resin 23 constituting the second region N2 in the joint part C1, so that the change in flexural rigidity due to the difference in the type of resin forming the outer layer 20 can be made gradual. As a result, the rigidity gap of the flexural rigidity in the vicinity of the joint part C1 is less likely to occur, so that the occurrence of kinking and breakage due to stress concentration can be suppressed.

Further, according to the multi-lumen tube 10 of the present embodiment, a wave pattern is formed on the second inner layer tube 50 side of the outer layer 20 in the joint part C1 (FIG. 3) between the first region N1 and the second region N2. Therefore, the change in the flexural rigidity of the outer layer 20 can be made gradual around the second inner layer tube 50. As a result, a rigidity gap is less likely to occur around the second inner layer tube 50, so that the crush resistance of the second inner layer tube 50 can be further improved. Further, as shown in FIG. 7D, the position of the second inner layer tube 50 inside the outer layer tube 203 is fixed by the entering resin 221. Therefore, as shown in FIG. 7E, when the outer layer 20 is formed by heating the outer layer tube 203, it is possible to prevent the second inner layer tube 50 from being pushed and displaced by the molten resin.

In particular, according to the multi-lumen tube 10 of the present embodiment, as shown in FIG. 3, the resin 22 (entering resin 221) has entered on both sides of the second inner layer tube 50 in the joint part C1 between the first region N1 and the second region N2, so as to form a wave pattern. As a result, the movement of the second inner layer tube 50 is restricted by the entering resin 221 on both sides of the second inner layer tube 50, so that the displacement of the second inner layer tube 50 can be further suppressed when the outer layer 20 is formed.

Further, according to the multi-lumen tube 10 of the present embodiment, the entering resin 231 also forms a wave pattern in the second joint part between the second region N2 and the third region N3 of the outer layer 20, so that the joint area of the second joint part can be increased and the joint strength can be improved. Further, the entering resin 231 is formed to realize the gradual switching from the resin 23 constituting the second region N2 to the resin 24 constituting the third region N3 in the second joint part, so that it is possible to make it difficult for a rigidity gap to occur in the vicinity of the second joint part.

Further, in the catheter 1 of the present embodiment, the hardness H1 of the resin 22 of the first region N1 is lower than the hardness H2 of the resin 23 of the second region N2. According to this configuration, the rigidity can be gradually increased from the distal end to the proximal end of the catheter 1, so that the passage of the catheter 1 through a tubular organ such as a blood vessel can be improved. As described, the passage of the catheter 1 through a tubular organ such as a blood vessel can be improved by gradually increasing the flexural rigidity from the distal end portion to the proximal end portion thereof. In the catheter 1 of the present embodiment, the hardness H1 of the resin 22 of the first region N1 is lower than the hardness 112 of the resin 23 of the second region N2, so that the position where the flexural rigidity changes can be multi-staged in the axial direction of the catheter 1. As a result, the rigidity can be gradually increased from the distal end to the proximal end of the catheter 1, so that the passage of the catheter 1 through a tubular organ such as a blood vessel can be improved while suppressing the occurrence of a rigidity gap.

Second Embodiment

FIG. 10 is an explanatory view illustrating the vicinity of the joint part C1 of a multi-lumen tube 10A of the second embodiment. FIG. 10 corresponds to FIG. 4 for the first embodiment. In the multi-lumen tube 10 of the first embodiment, as shown in FIG. 4, on the first inner layer tube 30 side of the outer layer 20, the resin 22 of the first region N1 has not substantially entered the second region N2 in the joint part C1, forming no wave pattern. However, as in the multi-lumen tube 10A of the second embodiment shown in FIG. 10, the resin 22 of the first region N1 may enter the second region N2 to form a wave pattern in the joint part C1 on the first inner layer tube 30 side of the outer layer 20, as in the case of the second inner layer tube 50 side of the outer layer 20.

In this case, the joint area between the resin 22 of the first region N1 and the resin 23 of the second region N2 of the outer layer 20 can be further increased. Further, the entering resin 221 is disposed in a more balanced manner in the circumferential direction of the outer layer 20, so that the joint strength at the joint part C1 between the first region N1 and the second region N2 can be further improved. As described above, according to the multi-lumen tube 10A of the present embodiment, on the first inner layer tube 30 side of the outer layer 20, the resin 22 of the first region N1 may or may not enter the second region N2 in the joint part C1. However, the resin preferably enters also on the first inner layer tube 30 side.

Third Embodiment

FIG. 11 is an explanatory view illustrating the vicinity of the joint part C1 of the multi-lumen tube 10B of the third embodiment. FIG. 11 corresponds to FIG. 3 for the first embodiment. In the multi-lumen tube 10 of the first embodiment, as shown in FIG. 3, on the second inner layer tube 50 side of the outer layer 20, the resin 22 of the first region N1 enters the second region N2 on both sides of the second inner layer tube 50 to form a wave pattern. However, as in the multi-lumen tube 10B of the third embodiment shown in FIG. 11, on the second inner layer tube 50 side of the outer layer 20, the resin 22 of the first region N1 may enter the second region N2 on only one side of the second inner layer tube 50. Even in this case, since a wave pattern is formed by the portion where the resin 22 has entered the second region N2 (entering resin 221) and the portion where the resin 22 has not entered, the joint area can be more increased as compared with a case where the joint part C1 is linear. Accordingly, the joint strength at the joint part C1 between the first region N1 and the second region N2 can be improved.

As described above, according to the multi-lumen tube 10B of the present embodiment, on the first inner layer tube 30 side of the outer layer 20, the resin 22 may enter the second region N2 on both sides of the second inner layer tube 50, or the resin 22 may enter the second region N2 only on one side of the second inner layer tube 50. However, it is preferable that the resin 22 of the first region N1 enters the second region N2 to form a wave pattern on both sides of the second inner layer tube 50. On the outer peripheral surface of the outer layer 20, the resin 22 may enter the second region N2 only in the portion where the second inner layer tube 50 is located, or may enter the second region N2 in the portion where the second inner layer tube 50 is located and on both sides thereof.

Fourth Embodiment

Figure 12A:
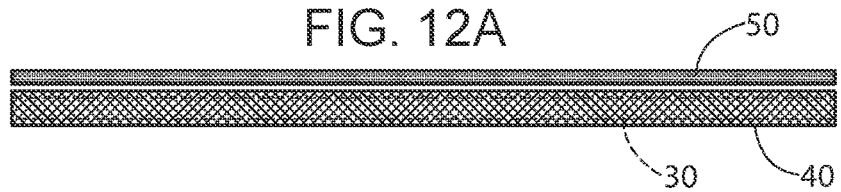
FIGS. 12A-12F are explanatory diagrams illustrating the production steps of the fourth embodiment.
Figure 12B:
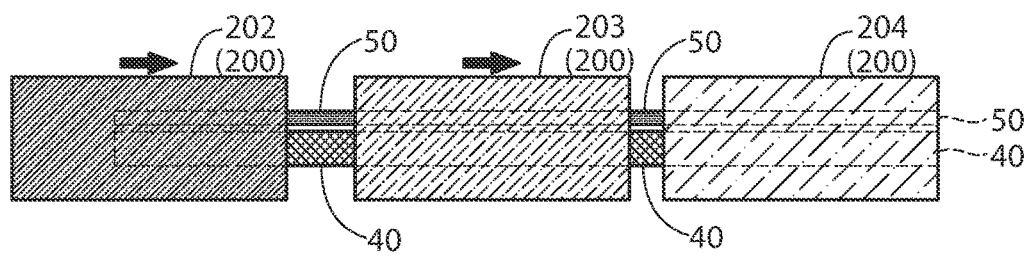
Figure 12C:
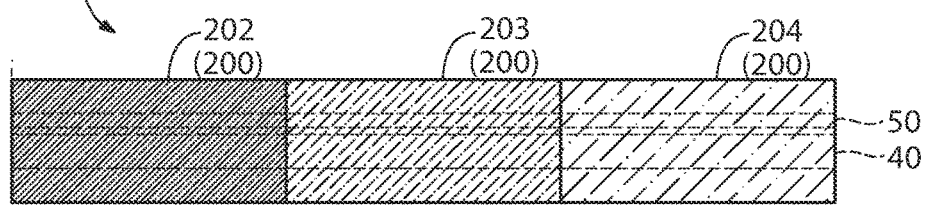

FIGS. 12A-12F illustrate the production steps of a multi-lumen tube 10C of the fourth embodiment. FIGS. 12A-12F correspond to FIGS. 7A-7F for the first embodiment. The steps shown in FIGS. 12A to 12C are the same as the steps shown in FIGS. 7A to 7C. In the production steps of the multi-lumen tube 10 of the first embodiment, as shown in FIGS. 7D and 7E, the seven outer layer tubes 200 are heated in order from the outer layer tube on the distal end side. However, in the production steps of the multi-lumen tube 10C of the fourth embodiment shown in FIGS. 12A-12F, the seven outer layer tubes 200 are heated in order from the proximal end side to the distal end side. Specifically, here, the outer layer tube in the sixth region N6 (not shown), the outer layer tube in the fifth region N5 (not shown), the outer layer tube in the fourth region N4 (not shown), the outer layer tube 204 in the third region N3, the outer layer tube 203 in the second region N2, the outer layer tube 202 in the first region N1, and the outer layer tube in the distal end region N0 (not shown) are heated in this order.

Figure 12D:
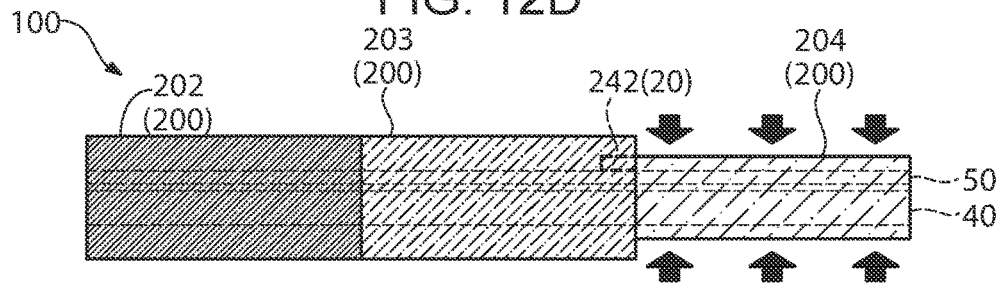

FIG. 12D shows a state in which the outer layer tube 204 is heated to melt the resin. When the outer layer tube 204 is heated to melt the resin, a part of the molten resin flows into the inside of the outer layer tube 203 adjacent on the distal end side. As a result, the entering resin 242 is formed. In particular, since a relatively large gap Sp (see FIG. 8) is formed on both sides of the second inner layer tube 50 inside the outer layer tube 203, the resin flows into the gap Sp to form the relatively large entering resin 242.

Figure 12E:
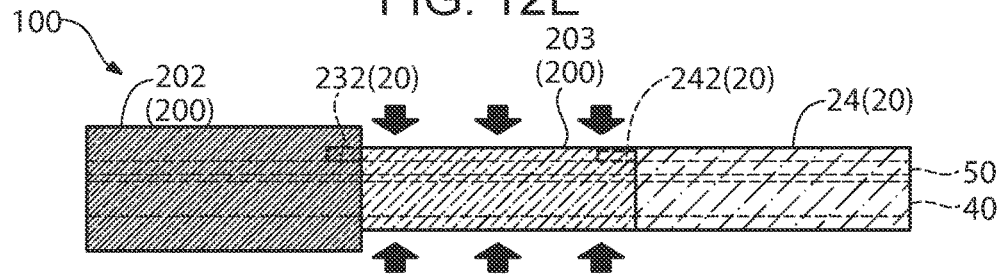
Figure 12F:
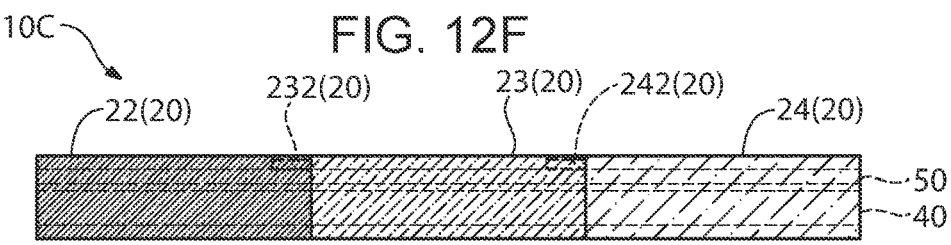

After the outer layer tube 204 is melted to form the third region of the outer layer 20, the outer layer tube 203 is heated to melt the resin as shown in FIG. 12E. At this time, a part of the molten resin flows into the inside of the outer layer tube 202 adjacent on the distal end side. As a result, the entering resin 232 is similarly formed. In this way, the seven outer layer tubes 200 are heated in order from the outer layer tube on the proximal end side, so as to complete the production of the multi-lumen tube 10C as shown in FIG. 12F, wherein the resin of each proximal end side region has entered the adjacent distal end side region.

As described above, according to the multi-lumen tube 10C of the present embodiment, as for the resin of each region constituting the outer layer 20, the resin constituting each region on the proximal end side may enter the region on the distal end side. Even in this case, the entering resin having entered from the proximal end side to the distal end side forms a wave pattern in the joint part between the two regions adjacent to each other of the outer layer 20, so that the joint area can be increased more than that in the case of the linear joint part. Accordingly, the joint strength at the joint part between the two adjacent regions can be improved. Further, in the joint part between the two adjacent regions, the change in flexural rigidity due to the difference in the type of resin can be made gradual. As a result, a rigidity gap of flexural rigidity in the vicinity of the joint part is less likely to occur, so that the occurrence of kinking and fracture due to stress concentration can be suppressed.

Fifth Embodiment

Figure 13A:
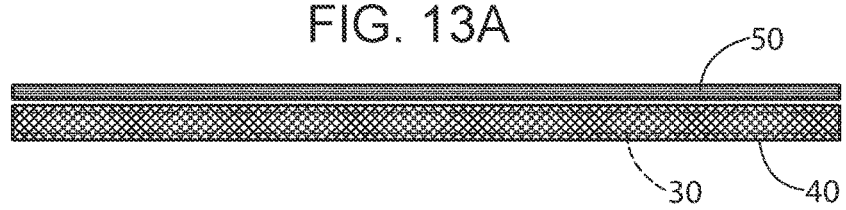
FIGS. 13A-13F are explanatory diagrams illustrating the production steps of the fifth embodiment.
Figure 13B:
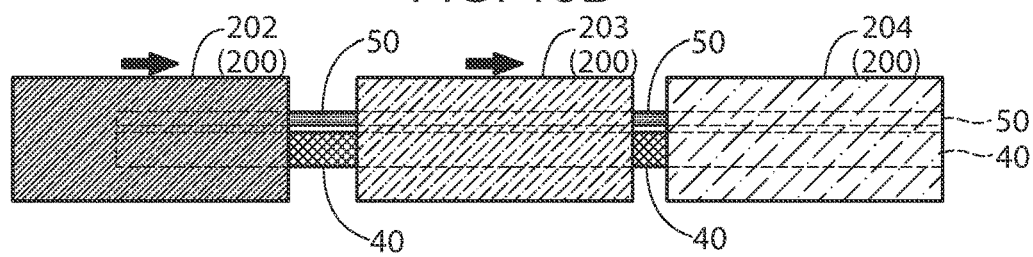
Figure 13C:
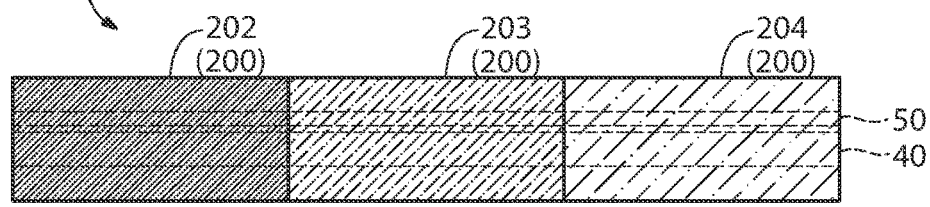

FIGS. 13A-13F illustrate the production steps of a multi-lumen tube 10D of the fifth embodiment. FIGS. 13A-13F correspond to FIGS. 7A-7F for the first embodiment. The steps shown in FIGS. 13A to 13C are the same as the steps shown in FIGS. 7A to 7C. In the production steps of the multi-lumen tube 10 of the first embodiment, the seven outer layer tubes 200 are heated in order from the outer layer tube on the distal end side. However, the order for heating the seven outer layer tubes 200 is not limited to the order from one end toward the other end of the assembly 100. The order for heating the seven outer layer tubes 200 can be arbitrarily set. Further, a plurality of the seven outer layer tubes 200 may be heated simultaneously as long as they are not adjacent to each other.

Figure 13D:
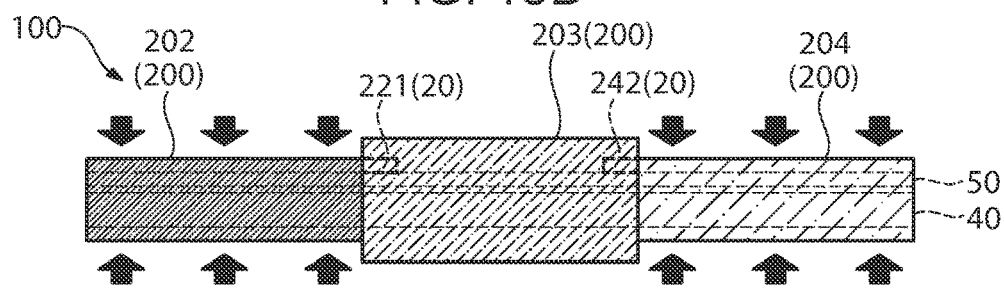
Figure 13E:
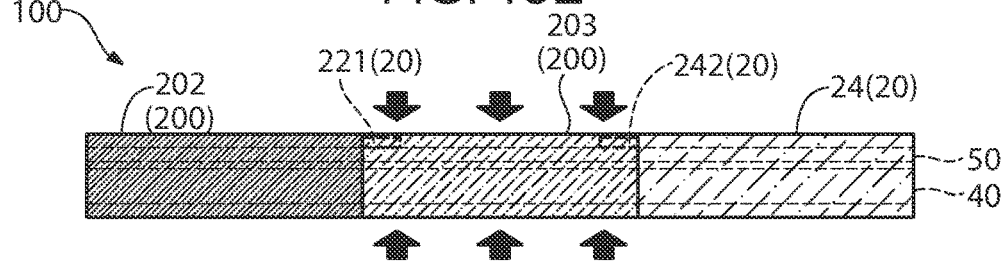

As shown in FIG. 13D, in the production steps of the multi-lumen tube 10D of the fifth embodiment, the outer layer tube 202 of the first region N1 and the outer layer tube 204 of the third region N3 are simultaneously heated, and then the outer layer tube 203 of the second region N2 is heated as shown in FIG. 13E. Next, although not shown, the outer layer tube of the distal end region N0 and the outer layer tube of the fifth region N5 are heated in order, and then the outer layer tube of the fourth region N4 and the outer layer tube of the sixth region N6 are heated simultaneously.

Figure 13F:
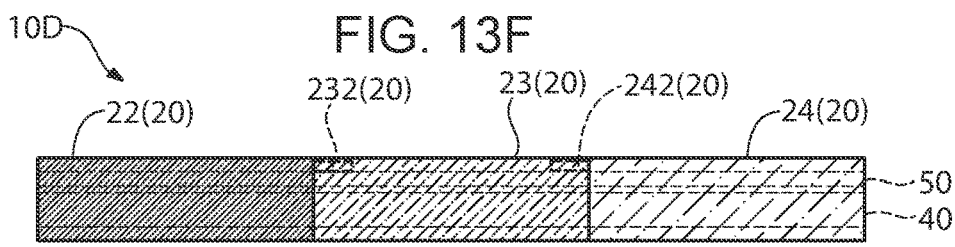

As shown in FIG. 13D, when the outer layer tube 202 is heated to melt the resin, a part of the molten resin flows into the inside of the outer layer tube 203 adjacent on the rear end side. As a result, the entering resin 221 is formed. Further, when the outer layer tube 204 is heated to melt the resin, a part of the molten resin flows into the inside of the outer layer tube 203 adjacent on the distal end side. As a result, the entering resin 242 is formed. After melting the outer layer tube 202 and the outer layer tube 204, the outer layer tube 203 is heated to melt the resin as shown in FIG. 13E. In this way, the outer layer tubes 202 and 204 on both sides of the outer layer tube 203 are heated before heating the outer layer tube 203, so that the production of the multi-lumen tube 10D is completed, wherein each resin from the first region N1 and the third region N3 has entered the second region N2, as shown in FIG. 13F.

As described above, according to the multi-lumen tube 10D of the present embodiment, the resin of each region constituting the outer layer 20 may enter the adjacent region on the distal end side or enter the adjacent region on the proximal end side. Even in these cases, in two regions adjacent to each other, the entering resin enters from one of the regions into the other region, so as to form a wave pattern in the joint part. As a result, the joint area can be increased and the joint strength at the joint part can be improved as compared with the case where the joint part is linear.

Sixth Embodiment

Figure 14:
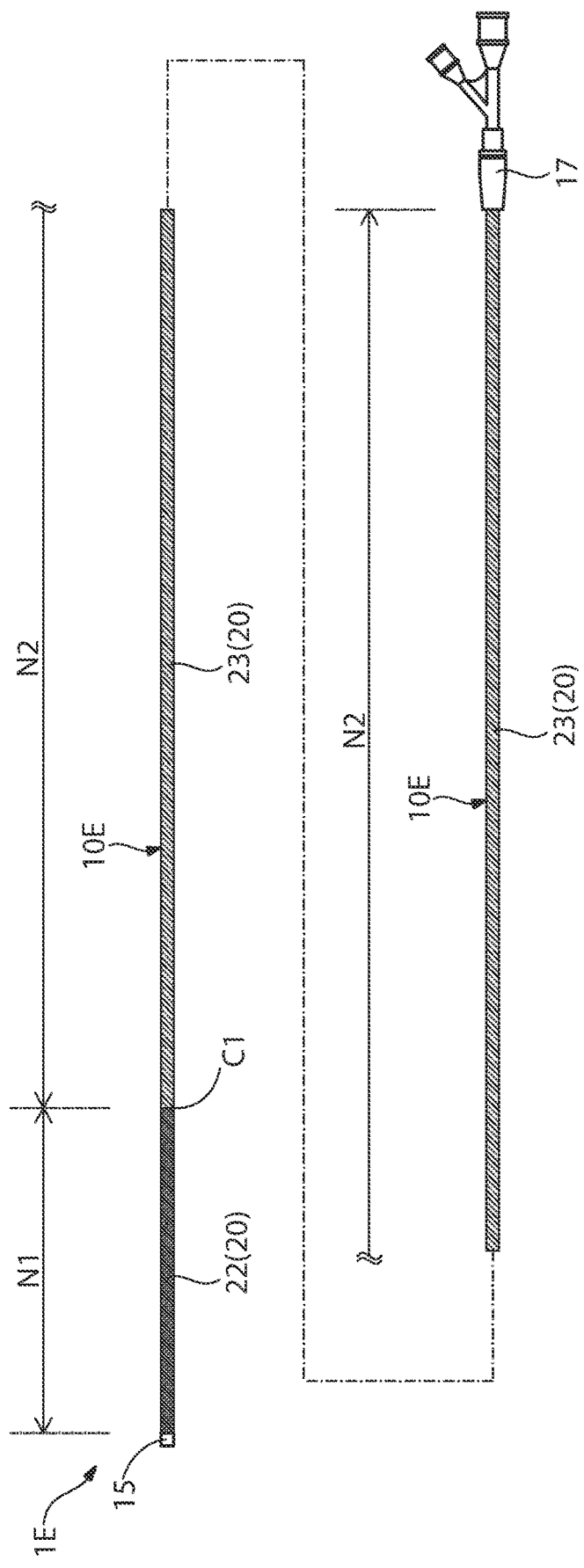
FIG. 14 is an explanatory view illustrating the appearance of the catheter of the sixth embodiment.

FIG. 14 is an explanatory view illustrating the appearance of the catheter 1E including a multi-lumen tube 10E of the sixth embodiment. FIG. 14 corresponds to FIG. 1 for the first embodiment. The outer layer 20 of the multi-lumen tube 10 of the first embodiment has seven regions N0 to N6 formed of resins having different properties from each other. However, the number of regions of the outer layer 20 of the multi-lumen tube 10 is not limited to 7, and can be any number of 2 or more. Further, in the first embodiment, an example in which the multi-lumen tube 10 is applied to a balloon catheter is shown, but the multi-lumen tube 10 is also applicable to a catheter other than the balloon catheter.

The sixth embodiment shown in FIG. 14 shows an example in which the multi-lumen tube 10E is applied to a catheter including no balloon. Further, the multi-lumen tube 10E of the present embodiment includes two regions formed of different resins in the outer layer 20. Here, the two regions are referred to as a first region N1 and a second region N2 in this order from the distal end side to the proximal end side of the outer layer 20. The distal end side of the first region N1 of the outer layer 20 is connected to the distal tip 15, and the proximal end side of the first region N1 is connected to the distal end side of the second region N2. The proximal end side of the second region N2 of the outer layer 20 is connected to the connector 17.

The outer layer 20 is configured such that the hardness H1 of the resin 22 forming the first region N1 and the hardness H2 of the resin 23 forming the second region N2 satisfy the following formula (2).

$$H1 < H2 \quad (2)$$

That is, the catheter 1 is configured so that the hardness of the resins of the outer layer 20 increases from the distal end side to the proximal end side. This makes it possible to improve the passage of the catheter 1 through a tubular organ such as a blood vessel. Similar to the first embodiment, in the joint part C1 between the first region N1 and the second region N2 of the outer layer 20, a wave pattern is formed by the resin 22 of the first region N1 having entered the second region N2. The configuration of the joint part C1 between the first region N1 and the second region N2 of the outer layer 20 is the same as that shown in FIGS. 3 and 4 for the first embodiment.

As described above, according to the multi-lumen tube 10E of the present embodiment, the number of types of resins constituting the outer layer 20, that is, the number of regions of the outer layer 20, can be any number of 2 or more. In any case, in two regions adjacent to each other, the entering resin enters from one of the regions to the other region, so as to form a wave pattern in the joint part. As a result, the joint area can be increased and the joint strength at the joint part can be improved as compared with the case where the joint part is linear.

7th Embodiment

Figure 15:
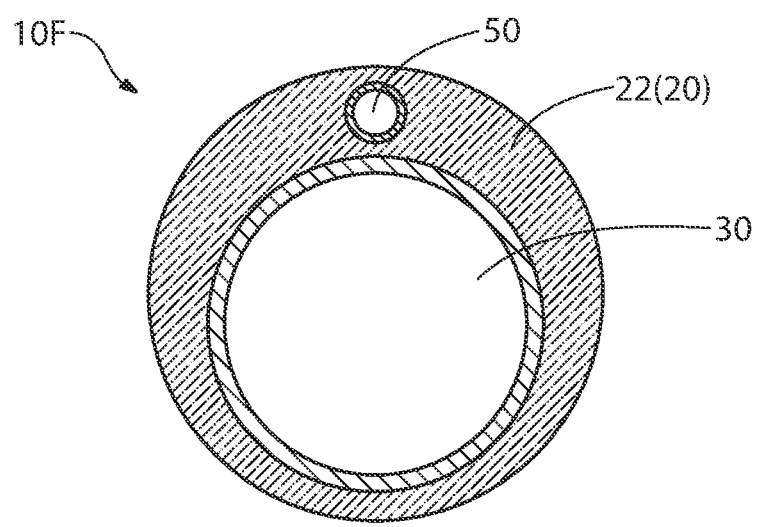
FIG. 15 is an explanatory view illustrating the multi-lumen tube of the seventh embodiment.

FIG. 15 is an explanatory view illustrating a transverse section of a multi-lumen tube 10F of the seventh embodiment. FIG. 15 corresponds to FIG. 2 for the first embodiment. In the multi-lumen tube 10 of the first embodiment, as shown in FIG. 2, the reinforcing body 40 is disposed on the outside of the first inner layer tube 30. However, like the multi-lumen tube 10F of the seventh embodiment shown in FIG. 15, the reinforcing body need not be disposed on the outside of the first inner layer tube 30. Even in this case, as in the case of the outer layer 20 of the first embodiment, if a wave pattern is formed in the joint part C1 between the first region N1 and the second region N2, the joint area can be increased as compared with a case where the joint part C1 is linear. Accordingly, the joint strength at the joint part C1 between the first region N1 and the second region N2 can be improved.

8th Embodiment

Figure 16:
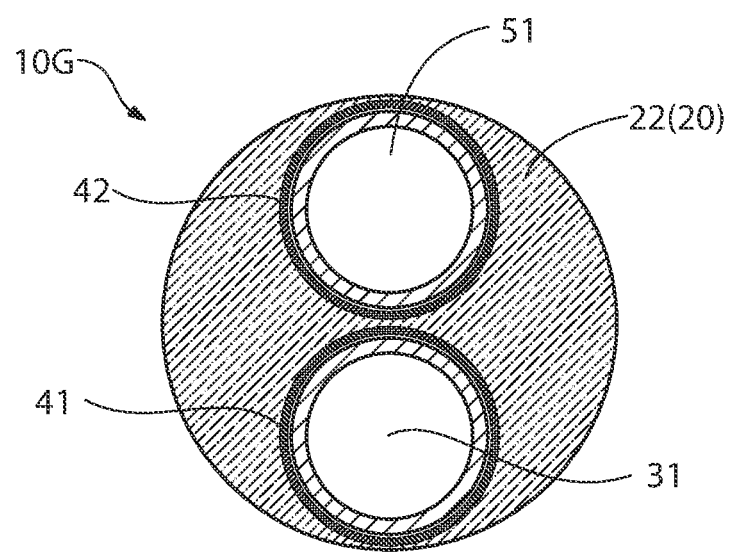
FIG. 16 is an explanatory view illustrating the multi-lumen tube of the eighth embodiment.

FIG. 16 is an explanatory view illustrating a transverse section of a multi-lumen tube 10G of the eighth embodiment. FIG. 16 corresponds to FIG. 2 for the first embodiment. In the multi-lumen tube 10 of the first embodiment, as shown in FIG. 2, the outer diameter of the second inner layer tube 50 is smaller than the outer diameter of the first inner layer tube 30. However, as in the multi-lumen tube 10G of the eighth embodiment shown in FIG. 16, the outer diameter of a second inner layer tube 51 may be equal to the outer diameter of a first inner layer tube 31. Even in this case, when the multi-lumen tube 10G is produced, a gap is formed between the second inner layer tube 51 and the first inner layer tube 31 and the outer layer tube 200 (see FIG. 8). Hence, the molten resin of the outer layer tube can be poured into the gap, so as to form an entering resin. As a result, similar to the outer layer 20 of the first embodiment, a wave pattern is formed in the joint part C1 between the first region N1 and the second region N2 to increase the joint area, and thus the joint strength at the joint part C1 can be improved. As shown in FIG. 16, reinforcing bodies 41 and 42 may be disposed on the outer peripheries of the first inner layer tube 31 and the second inner layer tube 51, respectively, or one reinforcing body may not be disposed on at least one of the outer peripheries of the first inner layer tube 31 and the second inner layer tube 51.

9th Embodiment

Figure 17:
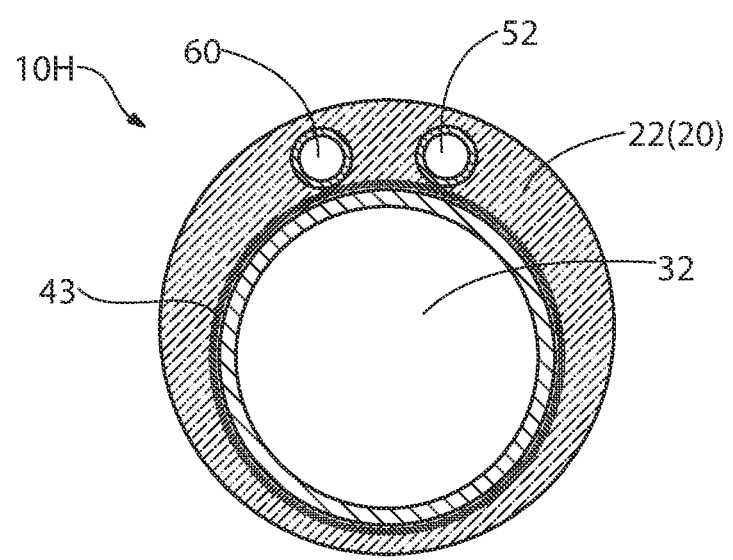
FIG. 17 is an explanatory view illustrating the multi-lumen tube of the ninth embodiment.

FIG. 17 is an explanatory view illustrating a transverse section of a multi-lumen tube 10H of the ninth embodiment. FIG. 17 corresponds to FIG. 2 for the first embodiment. As shown in FIG. 2, the multi-lumen tube 10 of the first embodiment includes two inner layer tubes (the first inner layer tube 30 and the second inner layer tube 50). However, the number of inner layer tubes included in the multi-lumen tube 10 is not limited to 2, and can be any number. For example, as in the multi-lumen tube 10H of the ninth embodiment shown in FIG. 17, three inner layer tubes, a first inner layer tube 32, a second inner layer tube 52, and a third inner layer tube 60, may be included. Even in this case, at the time of production of the multi-lumen tube 10H, a gap is formed between the three inner layer tubes 32, 52, 60 and the outer layer tubes 200 (see FIG. 8). Hence, the molten resins of the outer layer tubes 200 can be poured into the gap, so as to form entering resins. As a result, similar to the outer layer 20 of the first embodiment, a wave pattern is formed in the joint part C1 between the first region N1 and the second region N2 to increase the joint area, so that the joint strength at the joint part C1 can be improved.

Modification Example of the Embodiments

The disclosed embodiments are not limited to the above-described embodiments, and can be implemented in various aspects without departing from the gist thereof. For example, the following modification examples are also possible.

Modification Example 1

In the first and fourth embodiments (FIGS. 7A-7F and 12A-12F), the outer layer tubes 200 are heated one by one in the production steps of the multi-lumen tubes 10 and 10C, and in the fifth embodiment (FIGS. 13A-13F), two outer layer tubes 200 are heated simultaneously. However, in the production steps, three or more outer layer tubes 200 may be heated simultaneously. Even in this case, a wave pattern can be formed in the joint part C1 between the first region N1 and the second region N2 by the entering resin, and the joint area can be increased. Note that it is preferable to simultaneously heat a plurality of outer layer tubes 200 that are not adjacent to each other rather than the outer layer tubes 200 that are adjacent to each other because this facilitates the formation of an entering resin.

Modification Example 2

In the above embodiment, the number of inner layer tubes (number of lumens) included in the multi-lumen tube ranges from 2 to 3. However, the number of inner layer tubes included in the multi-lumen tube is not limited to 2 to 3. The multi-lumen tube may include four or more inner layer tubes. The present embodiment is also applicable to a single lumen tube having one lumen. Even in this case, a wave pattern can be formed in the joint part C1 between the first region N1 and the second region N2 by the entering resin, and the joint area can be increased.

Modification Example 3

The number of types of resins constituting the outer layer 20, that is, the number of regions of the outer layer 20 may be 8 or more. Further, when the outer layer 20 has a plurality of regions, the hardness of the resin constituting the region on the distal end side of the catheter 1 may be higher than the hardness of the resin constituting the region on the proximal end side. Further, the entering resin may not be covered by the resin on the side the other resin has entered, and may be exposed. Further, the outer diameter of the multi-lumen tube may be constant or may be varied in the axial direction.

Modification Example 4

In the multi-lumen tube of the above-described embodiment, a visible wave pattern is formed in the joint part C1 of the outer layer 20. However, the wave pattern formed in the joint part C1 may not always be visible. Even in this case, if the joint area can be increased by the entering resin, the joint strength can be improved. Further, the shape of the pattern formed in the joint part C1 by the entering resin may not always be a wave pattern. For example, it may have a chevron shape or a rectangular shape. Even in these cases, the joint strength can be improved by the entering resin.

Modification Example 5

The multi-lumen tube of the above-described embodiment includes no coil body on the outside of the inner layer tubes. However, the multi-lumen tube may include a coil body on the outside of the inner layer tubes. Further, the outer diameters of the inner layer tubes may be constant or may be varied in the axial direction.

Modification Example 6

In the outer layer 20 of the present embodiment, regions are formed of different types of resins. However, the regions may be of the same type of resin and may be configured such that the amounts of the materials to be kneaded into the resin are different from each other. Even in this case, since the hardness of the resin can be varied, the rigidity can be gradually increased from the distal end side to the proximal end side of the multi-lumen tube 10. At least two or more regions among the regions of the outer layer 20 may be formed of the same type of resin and have the same hardness. For example, two adjacent regions may be formed of the same type of resin. Even in this case, since the joint area is increased by the entering resin, the joint strength can be increased. Further, when the resin melted by heating one of the outer layer tubes 200 is poured around an inner layer tube, it is possible to prevent the inner layer tube from being displaced by the molten resin. When the two adjacent regions of the outer layer 20 are formed of different types of resins, the change in rigidity in the joint part C1 can be made gradual.

Modification Example 7

In the outer layer 20 of the present embodiment, the order of heating matches the order of melting the resin of each region of the outer layer 20. However, the resin of the adjacent region may be melted first despite of the order of heating, and thus this resin of the adjacent region may flow into the region where the heating is started previously to form a wave pattern. For example, when heating is started from the proximal end side of the catheter 1, the resin having lower hardness in the adjacent region on the distal end side melts earlier than the resin having higher hardness on the proximal end side, and flows into the proximal end side region, and thus a wave pattern may be formed. Even in that case, the change in rigidity in the joint part C1 can be made gentle as a result of flowing of the resin with low hardness into the region of the resin with high hardness.

Modification Example 8

The catheter 1 of the present embodiment may have or may not have a resin coating formed outside the outer layer 20. When a resin coating is formed outside the outer layer 20, different types of resin films may be formed, or the same type of resin films may be formed in at least a part of each region of the outer layer.

Modification Example 9

The configuration of this embodiment is also applicable to medical devices other than balloon catheters. For example, the configuration of the present embodiment is also applicable to a multi-lumen catheter, a single-lumen catheter, a dilator, an endoscope, a guide wire, and the like without a balloon. In addition, parts of each configuration of the multi-lumen tube illustrated in the first to ninth embodiments can be appropriately combined and can be appropriately removed.

Although the aspects have been described above based on the embodiments and modification examples, the embodiments of the above-described aspects are described herein to facilitate the understanding of the present aspects, and do not limit the present aspects. These aspects may be modified or improved without departing from their spirit and claims, and these aspects include their equivalents. In addition, if the technical features are not described as essential in the present specification, they may be deleted as appropriate.

DESCRIPTION OF REFERENCE NUMERALS

1 Catheter
10, 10A-H Multi-lumen tube
15 Distal tip
16 Balloon
17 Connector
20 Outer layer
21-27 Resin
30-32 First inner layer tube
40, 41 Reinforcing body
50-52 Second inner layer tube
60 Third inner layer tube
100 Assembly
200, 202-204 Outer layer tube
221, 231, 232, 242 Entering resin

What is claimed is:

1. A medical multi-lumen tube comprising:
a plurality of inner layer tubes including:
   a first inner layer tube; and
   a second inner layer tube positioned outside the first inner layer tube, the second inner layer tube having a smaller outer diameter than the first inner layer tube; and
an outer layer covering the plurality of inner layer tubes, wherein:
the outer layer comprises a first region and a second region that are connected to each other in an axial direction of the outer layer at a first joint part,
the first region comprises a first resin, and the second region comprises a second resin having different properties than the first resin;
in the outer layer, the first resin extends into the second region on both sides of the second inner layer tube in a circumferential direction so as to form a wave pattern in the first joint part between the first and second regions at least on a side of the outer layer in the circumferential direction where the second inner layer tube is located;
an amount of the first resin extending into the second region is larger on a side of the outer layer that is in contact with the first inner layer tube than on an outer side of the outer layer in a thickness direction of the outer layer; and
the first and second resins do not form the wave pattern in the first joint part between the first and second regions on a side of the outer layer in the circumferential direction where the second inner layer tube is not located.

2. The medical multi-lumen tube according to claim 1, wherein:

the outer layer comprises a third region formed of a third resin having properties different from those of the second resin, the second region and the third region are connected at a second joint part, and in the second joint part, the second resin extends into the third region so as to form a wave pattern.

3. A catheter comprising:

the medical multi-lumen tube according to claim 1, wherein:

the first region is closer than the second region to a distal end side of the catheter, and a hardness of the first resin is lower than a hardness of the second resin.

4. A catheter comprising:

the medical multi-lumen tube according to claim 2, wherein:

the first region is closer than the second region to a distal end side of the catheter, and a hardness of the first resin is lower than a hardness of the second resin.

5. A method for producing the medical multi-lumen tube according to claim 1, the method comprising:

covering a first part of the plurality of inner layer tubes with the first resin to form the first region of the outer layer, covering a second part of the plurality of inner layer tubes with the second resin to form the second region of the outer layer at a position adjacent to the first region in the axial direction of the outer layer, and connecting the first and second regions to each other in the axial direction by causing the first resin to flow into the second region in the joint part, thereby forming the wave pattern.

6. The medical multi-lumen tube according to claim 1, comprising a single one of the second inner layer tube.

* * * * *